United States Patent [19]
Koch et al.

[11] Patent Number: 4,552,977
[45] Date of Patent: Nov. 12, 1985

[54] PROCESS FOR THE PREPARATION OF (PHENOXY- OR BENZYL-)-PHENOXYPROPIONIC ACIDS AND THEIR ALKALI METAL SALTS

[75] Inventors: Manfred Koch, Eppstein; Peter Herbrechtsmeier, Hofheim am Taunus, both of Fed. Rep. of Germany

[73] Assignee: Hoechst Aktiengesellschaft, Frankfurt am Main, Fed. Rep. of Germany

[21] Appl. No.: 422,712

[22] Filed: Sep. 24, 1982

Related U.S. Application Data

[63] Continuation of Ser. No. 158,596, Jun. 11, 1980, abandoned.

[30] Foreign Application Priority Data

Dec. 16, 1978 [DE] Fed. Rep. of Germany ....... 2854492
Dec. 11, 1979 [DE] Fed. Rep. of Germany ....... 2949681

[51] Int. Cl.$^4$ ............................................. C07C 79/46
[52] U.S. Cl. ..................................... 562/435; 562/468; 562/471; 562/472; 260/465 D; 560/57; 560/61; 560/62
[58] Field of Search ............... 562/435, 468, 471, 472; 260/465 D; 560/57, 61, 62

[56] References Cited

U.S. PATENT DOCUMENTS 3,721,703 3/1973 Nahm et al. ..................... 562/435
4,134,753 1/1979 Horlein et al. .................. 562/435

FOREIGN PATENT DOCUMENTS 0003562 8/1979 European Pat. Off. ........... 562/586
2000174 8/1969 France .............................. 562/435

Primary Examiner—Paul J. Killos
Attorney, Agent, or Firm—Curtis, Morris & Safford

[57] ABSTRACT

Process for the preparation of (phenoxy- or benzyl-)-phenoxypropionic acids and the alkali metal salts thereof by adding a double molar amount of an aqueous alkali hydroxide to a boiling mixture of a (benzyl- or phenoxy-)-phenol and 2-chloropropionic acid (ester), with simultaneous azeotropic distillation of the water introduced or formed in the reaction.

8 Claims, No Drawings

PROCESS FOR THE PREPARATION OF (PHENOXY- OR BENZYL-)-PHENOXYPROPIONIC ACIDS AND THEIR ALKALI METAL SALTS

This is a continuation of application Ser. No. 158,596 filed June 11, 1980 now abandoned.

The present invention relates to a process for the preparation of (phenoxy- or benzyl-)-phenoxypropionic acids of the formula

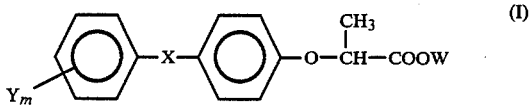

in which
Y is a radical selected from the group of halogen, preferably chlorine or bromine, $CF_3$, $NO_2$ or CN,
X is oxygen or —$CH_2$—,
W is hydrogen, sodium or potassium, and
m is 1 or 2, and the optically active D-isomers thereof.

It is known that alkyl- and/or halogen-substituted phenoxy-alkanecarboxylic acids which are of great economic importance as hormone-type herbicides are obtained by reaction of alkali phenolates with alkali salts of corresponding 2-haloalkanecarboxylic acids.

The reaction is generally carried out by condensing alkali phenolate and alkali-2-haloalkanecarboxylate in a molar ratio of 1:1 in water as solvent or diluent (see G. Erfurt et al., Chem. Technik 15 (1964), No. 4, p. 199; GDR Patent Specifications Nos. 64,279, 64,972, 64,723).

Because of inevitable side reactions, mainly hydrolysis of haloalkanecarboxylate to hydroxyalkanecarboxylate, the yield is not satisfactory (70–80% of theory). The yield is even more reduced if the reaction is transferred from 2-chloroacetic acid to higher 2-chloroalkanecarboxylic acids such as 2-chloropropionic and 2-chlorobutyric acid (German Patent No. 1,153,762).

The yield of hormone-type herbicides can be increased by suppressing the hydrolysis to a certain extent, for example according to the following methods:

(a) Use of anhydrous reactants (U.S. Pat. No. 2,651,659). Although considerably increased yields are obtained according to this process, it is not suitable for application on an industrial scale because preparation of anhydrous agents, especially of alkali metal salts of 2-haloalkanecarboxylic acids sensitive to hydrolysis, is difficult and expensive,
large volumes of organic solvents are required,
solids and suspensions are difficult to dose, and
considerable amounts of lactates are formed as undesirable by-products because of side reaction of phenoxyalkanecarboxylic acid salts with haloalkanecarboxylic acid salt.

(b) Partial replacement of water as solvent and diluent by high-boiling alcohols (German Patent No. 1,153,762, U.S. Pat. No. 2,914,558, USSR Patent No. 187,766, Japanese Patent Application No. 48,705/65), hydrocarbons (U.S. Pat. No. 2,480,817), or excess free phenol (U.S. Pat. No. 4,035,496, GDR Patent No. 50,622).

(c) Use of alkali metal phenolate in an excess of up to 100%, relative to 2-haloalkanecarboxylic acid salt, in order to increase the speed of the main reaction as compared to that of the side reaction (U.S. Pat. Nos. 4,035,416 and 3,257,453, German Patent No. 1,153,762, Japanese Patent Publication No. 74/24463).

(d) Reduction of the water amount present in the reaction mixture by distilling off water during the reaction (U.S. Pat. No. 4,035,416).

All processes for the preparation of hormone-type herbicides previously known have the following characteristic features in common:

(1) The amount of phenol to be used in the reaction is introduced into the reaction vessel in the form of alkali phenolate, and 2-haloalkanecarboxylic acid salt is added in one portion, in dosed amounts or continuously. In some cases, the total alkali amount required is introduced as excess alkali phenolate or as a mixture of alkali phenolate and alkali hydroxide, and free 2-haloalkanecarboxylic acid is added.

(2) The phenol component is not reacted quantitatively.

Separation and recovery of unreacted phenol is required after completion of the reaction.

However, (phenoxy- or benzyl-) phenoxypropionic acids of the formula I cannot be obtained industrially in a similar manner, because the starting phenoxy-, or benzyl-phenols cannot be separated from the compounds of the formula I except by complicated and time-consuming purification operations resulting in great losses.

For the preparation of the formula I compounds various process variations have been described which do not lead to quantitative yields. For example, German Offenlegungsschrift No. 16,68,896 describes among others the reaction of alpha-haloalkanecarboxylic acids with phenoxyphenols in aqueous strongly alkaline solution. When operating according to this method, which corresponds to the early state of hormone-type herbicide manufacture, by condensing phenoxyphenols with a 20 molar % excess of 2-chloropropionic acid in an aqueous, strongly alkaline solution, a yield of only 82% of theory is obtained. A conversion rate of more than 95% of the phenol component is achieved only with a considerably increased excess of 2-chloropropionic acid (more than 40%). Such a process is not suitable for quantitatively converting phenols of the formula II on an industrial scale.

Improvement of this reaction by replacing water as solvent or diluent by a hydrocarbon such as toluene or xylene and azeotropic distillation of water during the reaction (as described in (b) and (d) above) likewise does not result in quantitative yields. Thus, use of an excess of 20% of 2-chloropropionic acid (relative to the amount of phenol used) yields a conversion rate of 92–93% of the phenol component only.

The preparation of optically active D-isomers of the compounds of the formula I presents particular difficulties.

The usual racemate separation of optically inactive 2-phenoxypropionic acids by means of optically active auxiliary bases is not suitable for production on an industrial scale since fractional crystallization which is required in this process necessitates complicated operations and results in high losses. Moreover, the reaction yields the undesired L-enantiomer in stoichiometric amounts which for all practical purposes is lost for further reactions since it cannot be reconverted to a cleavable racemate.

The method described in German Offenlegungsschrift No. 27,58,002, starting from 2-methane-sulfonyloxypropionic or toluenesulfonyloxypropionic acid derivatives, yields derivatives of the intended 2-phenoxypropionic acids from which the methanesulfonyl or toluenesulfonyl group has to be split off by alkaline or acidic saponification. This reaction step bears a high risk of racemization of the D-enantiomer obtained.

This, too, applies for the reaction of substituted phenols with optically active 2-bromopropionic acid derivatives in organic solvents such as acetone, methylethylketone or acetonitrile in the presence of a base (H. J. Nestler and H. Bieringer, Zeitschr. f. Naturforsch. 1980, in the press).

Moreover, the optically active 2-sulfonyloxypropionic and 2-bromopropionic acid derivatives are available only to a limited extent. On the other hand, optically active starting products easily obtainable on a large scale are L-2-chloropropionic acid alkyl esters, especially the methyl ester. However, the reaction of the latter with the phenols in organic solvents such as acetone, methylethylketone or acetonitrile in the presence of organic or inorganic bases is incomplete and therefore unfit for practical application. A nearly quantitative yield is obtained by reacting an alkali phenolate with 2-chloropropionic acid ester in high-boiling organic solvents such as toluene, xylene or chlorobenzene and subsequent saponification to give the acid; however, this reaction results in nearly complete racemization when carried out with optically active esters.

When using alkali salts of optically active 2-chloropropionic acid instead of esters the optical activity is substantially maintained; however, preparation of these salts by saponification of the L-2-chloropropionic acid esters (sole substances of industrial availability) is likewise problematic because of racemization. Moreover, in a side reaction to the ester saponification, saponification of the chlorine atom in alpha-position occurs with formation of lactic acid.

In German Patent No. 1,543,841, a process for the manufacture of D-phenoxypropionic acids is described according to which alkali salts of L-2-chloropropionic acid are formed in situ and reacted with phenolates, thus preventing racemization. This process requires maintaining narrow temperature limits of from 5° to 35° C. Due to the reactivity of the chloropropionic acid esters on the one hand and the tendency to crystallization on the other, however, these limits are inevitably exceeded with increasing batch volume. Thus, there is the risk of uncontrollable spontaneous reaction with overheating. Moreover, the water remaining in the reaction mixture according to the process of the patent prevents complete conversion of the reactants, so that considerable amounts of phenol remain in the final products.

Surprisingly, the disadvantages of the above processes are overcome by the process of the invention by which compounds of the formula I with yields of more than 99%, and the D-isomers thereof with yields of more than 95% are obtained with high optical purity.

The process comprises adding to a solution of a phenol of the formula II

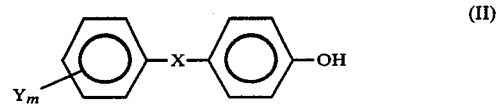

in which Y and m are as defined above, and an at least equimolar amount of 2-chloropropionic acid or 2-chloropropionic acid lower alkyl ester of the formula III

in which R is hydrogen or $(C_1-C_4)$-alkyl, in an organic solvent forming an azeotropic mixture with water, an about double molar amount, relative to III, or a slight excess thereover, of an aqueous alkali hydroxide, at boiling temperature, distilling off the water introduced or formed during the reaction as an azeotropic mixture, and optionally converting the alkali salts of the formula I obtained to the free acids by acidification.

For quantitative conversion (>99.5%) of the phenoxyphenols or benzylphenols of the formula II it is advantageous to add an at least 10% excess of compound III relative to the phenol amount used; generally, an excess of 12 to 20% is used.

The reaction is generally carried out at temperatures of from 80° to 130° C., preferably 90° to 120° C.

The process is described in detail as follows:

The starting and 2-chloropropionic acid or its ester are dissolved in an organic solvent forming an azeotropic mixture with water, for example toluene, xylene, chlorobenzene or dichlorobenzene. A 20–60%, preferably 30–50%, aqueous alkali hydroxide solution is then added, if desired at a reduced pressure, to the solution while simultaneously distilling off water.

Depending on the solvent, the reaction is carried out under normal or reduced pressure. The reduced pressure to be applied furthermore depends on the reaction temperature. It is recommended to carry out the reaction at a temperature of no less than 80° C., because otherwise the reaction would proceed too slowly, so that generally the pressure is not less than 200 mbar. In the case of xylene as solvent and a reaction temperature of 110° C., the pressure is about 500 mbar.

For the preparation of optically active D-isomers of the formula I, L-2-chloropropionic acid or its esters are used as starting material.

Per mol of phenol, about 1.1 to 1.4 mols, preferably 1.1 to 1.2 mols, of chloropropionic acid (ester), preferably chloropropionic acid methyl ester, and 2.2 to 2.8 mols, preferably 2.2 to 2.5 mols, of alkali hydroxide are used. Preferred alkali hydroxides are NaOH and KOH. Feed rate and reaction temperature are adjusted in such a manner that the total amount of water introduced and formed in the reaction corresponds substantially to the amount of water removed by azeotropic distillation. The alcohol formed by saponification of the ester, preferably methanol, is distilled off with the water.

The addition of alkali hydroxide solution being complete, stirring is continued for about 15 minutes at constant reaction temperature. The alkali salts of formula I can be directly converted to acid derivatives (for example esters) or to the free acids by acidification.

The compounds of the formula I obtained according to the invention are highly active weed herbicides or intermediates for other acid derivatives, for example esters, which are likewise very efficient, selective weed herbicides (German Offenlegungsschriften Nos. 22,23894; 24,33,067; 26,01,548, 24,17,487 and 27,58,002).

The yields are above 98%, in many cases above 99.5%. The degree of optical purity of the D-enantiomers is not more than 25% below that of the optically active 2-chloropropionic acid esters used. The optical purity in percent is calculated as follows: % content D-form minus % content L-form=optical purity.

The process of the invention differs from the known process in the art in that free phenoxyphenols or benzylphenols are used. By the addition of sodium hydroxide solution only, as much phenolate is formed as can immediately react with 2-chloropropionate, thus preventing an excess of alkali in the reaction mixture. Losses of compound III due to hydrolysis are thereby considerably reduced.

The following examples illustrate the invention. All parts are by weight unless otherwise stated.

Example 1

2-[4'-(2",4"-Dichlorophenoxy)-phenoxy]-propionic acid 208 parts of 50% sodium hydroxide solution are added portionwise at about 90° C. and at a reduced pressure of 270 mbar to a solution of 255 parts of 4-(2',4'-dichlorophenoxy)-phenol and 132 parts of 2-chloropropionic acid in 1,200 parts of xylene. By distilling off the water present in the reaction mixture, the reaction temperature is maintained at 90° C. The addition being complete, stirring is continued for 15 minutes at this temperature, subsequently the batch is brought to normal pressure. 400 Parts of water are then added, and stirring is continued for 10 minutes at 85° C. The batch is subsequently acidified at this temperature with 120 parts of phosphoric acid, and stirring is continued for 10 minutes. After elimination of the water phase via a separating funnel, xylene is distilled off under a pressure of 80 mbar, and the solids are dried at 60° C. and 250 mbar. 327 Parts of 2-[4'-(2,4-dichlorophenoxy)-phenoxy]-propionic acid are obtained. The content of pure final product is 99.5%, corresponding to a yield of 99.5% of theory. The residual amount of 4-(2',4'-dichlorophenoxy)-phenol is 0.3%.

EXAMPLE 2

2-[4'-(2",4"-Dichlorophenoxy)-phenoxy]-propionic acid

To a stirred solution of 127.5 parts of 4-(2',4'-dichlorophenoxy)-phenol and 69.2 parts of 2-chloropropionic acid methyl ester in 650 parts of xylene, 100 parts of 50% sodium hydroxide solution are added dropwise at about 110° C. and 500 mbar while simultaneously distilling off the azeotropic mixture of water and methanol. The addition being complete, stirring is continued for 15 minutes at 110° C. Work-up is as described in Example 1. 163.3 Parts of 2-[4'-(2",4"-dichlorophenoxy)-phenoxy]propionic acid are obtained. The content of pure final product is 99.8%, corresponding to 99.6% of theory. The residual amount of 4-(2',4'-dichlorphenoxy)-phenol is 0.15%.

EXAMPLE 3

D-2-[4-(2,4-dichlorophenoxy)-phenoxy]-propionic acid

Within about 1 hour, 77.7 g of 51.5% sodium hydroxide solution (1.0 mol) are added at 110° C. and 500 mbar and with vigorous stirring to a solution of 102 g (0.4 mol) of 4-(2,4-dichlorophenoxy)-phenol and 56.35 g (0.46 mol) of L-2-chloropropionic acid methyl ester in 450 ml of xylene. The azeotropic mixture of methanol formed and water introduced or formed is continuously distilled off.

The addition being complete, stirring is continued for 15 minutes at 110° C. and 500 mbar and the reactor is brought to normal pressure. At 90° C. first 100 ml of water are added and then the D-2-[4-(2,4-dichlorophenoxy)-phenoxy]-propionic acid is set free with dilute sulfuric acid. After separation of the water phase and distillation of xylene under reduced pressure, 129.8 g (99% of th.) of D-2-[4-(2,4-dichlorophenoxy)-phenoxy]-propionic acid are obtained with a purity of 98.8% according to gas chromatography. The residual amount of 4-(2,4-dichlorophenoxy)-phenol is 0.3%.

The optical purity is evaluated after conversion to the methyl ester. The optical rotation of the product obtained is $[\alpha]_D^{22}=21.14$, corresponding to an optical purity of 76%.

When using an L-chloropropionic acid ester having an optical purity of 95% (corresponding to 97.5% of L-form), the following compounds are obtained with optical purity degrees of more than 70% (corresponding to 85% of D-form):

D-2-[4-(4-chlorophenoxy)-phenoxy]-propionic acid
D-2-[4-(2,4-dichlorophenoxy)-phenoxy]-propionic acid
D-2-[4-(4-trifluoromethylphenoxy)-phenoxy]-propionic acid
D-2-[4-(2,4-dichlorobenzyl)-phenoxy]-propionic acid
D-2-[2-chloro-4-trifluoromethylphenoxy)-phenoxy]-propionic acid
D-2-[4-(4-bromo-2-chlorophenoxy)-phenoxy]-propionic acid, and the Na and K salts.

What is claimed is:

1. A process for the preparation of phenoxy- or benzyl-phenoxypropionic acid and the alkali metal salts thereof having the formula

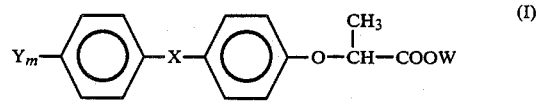

wherein
Y is a radical selected from the group consisting of halogen, $CF_3$, $NO_2$ and $CN$,
X is oxygen or $CH_2$,
W is hydrogen, sodium or potassium, and
m is 1 or 2, and optically active D-isomers thereof, consisting essentially of dissolving in an organic solvent a phenol having the formula

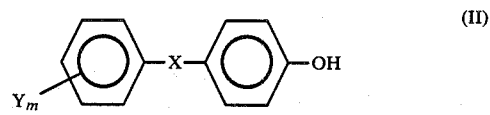

wherein Y and m are as defined above and at least an equimolar amount of 2-chloropropionic acid or 2-chloropropionic acid lower alkyl ester having the formula

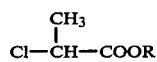

wherein R is hydrogen or $(C_1-C_4)$-alkyl to form an azeotropic mixture and water, adding at least twice the molar amount relative to said 2-chloropropionic acid or ester of an aqueous alkali hydroxide at its boiling temperature, removing by azeotropic distillation substantially all of the water introduced to or formed by the reaction and avoiding the formation of excess alkali by controlling the feed rate of said aqueous alkali hydroxide and the reaction temperature.

2. The process of claim 1 wherein Y is Cl or Br.

3. The process of claim 1 wherein 1.1 to 1.4 mols of 2-chloropropionic acid or ester are dissolved per mol of phenol.

4. The process of claim 1 or 3 wherein 2.2 to 2.8 mols of aqueous alkali hydroxide are added per mol of phenol.

5. The process of claim 1 wherein the alkali hydroxide is sodium hydroxide or potassium hydroxide.

6. The process of claim 1 wherein the phenol and chloropropionic acid or ester are reacted at a temperature in the range of 80° C. to 130° C.

7. The process of claim 1 wherein the phenol and chloropropionic acid or ester are reacted at a temperature in the range of 90° C. to 120° C.

8. The process of claim 1 wherein said alkali metal salts formed are converted to the corresponding free acid by acidification.

* * * * *